(12) United States Patent
Türker et al.

(10) Patent No.: US 7,168,467 B2
(45) Date of Patent: Jan. 30, 2007

(54) FILLING SYSTEM FOR AN ANESTHETIC EVAPORATOR

(75) Inventors: Ahmet Türker, Lübeck (DE);
Dirk-Stefan Reichert, Lübeck (DE);
Claus Bunke, Sereetz (DE)

(73) Assignee: Dräger Medical AG & Co. KGaA (DE)

( * ) Notice: Subject to any disclaimer, the term of this patent is extended or adjusted under 35 U.S.C. 154(b) by 0 days.

(21) Appl. No.: 11/253,538

(22) Filed: Oct. 19, 2005

(65) Prior Publication Data

US 2006/0130931 A1   Jun. 22, 2006

(30) Foreign Application Priority Data

Dec. 21, 2004   (DE) ............... 10 2004 061 392

(51) Int. Cl.
*B65B 1/04* (2006.01)

(52) U.S. Cl. .............. 141/292; 141/349; 141/363; 141/366; 141/375; 141/383

(58) Field of Classification Search ............... 141/18, 141/285, 290–292, 319, 346–351, 382, 383, 141/352, 363–366; 137/625.18; 251/321, 251/324, 229, 242–244
See application file for complete search history.

(56) References Cited

U.S. PATENT DOCUMENTS

| | | | | |
|---|---|---|---|---|
| 5,398,737 A | * | 3/1995 | Heinonen et al. | 141/285 |
| 5,832,972 A | * | 11/1998 | Thomas et al. | 141/360 |
| 5,915,427 A | * | 6/1999 | Grabenkort | 141/364 |
| 6,585,016 B1 | | 7/2003 | Falligant et al. | |

* cited by examiner

*Primary Examiner*—Timothy L. Maust
(74) *Attorney, Agent, or Firm*—McGlew & Tuttle

(57) ABSTRACT

A filling system for an anesthetic evaporator is improved such that an anesthetic-specifically coded adapter neck (5) of a bottle adapter (1) can be introduced into the filler neck of a filling device. An outer polygon (7) is provided on the bottle adapter and an inner polygon designed correspondingly thereto is provided on the filler neck as anesthetic-specific codings.

17 Claims, 4 Drawing Sheets

FILLING SYSTEM FOR AN ANESTHETIC EVAPORATOR

CROSS REFERENCE TO RELATED APPLICATIONS

This application claims the benefit of priority under 35 U.S.C. § 119 of German Patent Application 10 2004 061 392.3 Dec. 21, 2004 filed, the entire contents of which are incorporated herein by reference.

FIELD OF THE INVENTION

The present invention pertains to a filling system for an anesthetic evaporator.

BACKGROUND OF THE INVENTION

A filling system of the type has become known from U.S. Pat. No. 6,585,016 B1. To make it possible to fill liquid anesthetic into an anesthetic evaporator, a bottle adapter is necessary, which establishes the connection between the storage container for liquid anesthetic and the filling device at the anesthetic evaporator. A collet, which has two grooves for receiving an index collar arranged at the neck of the storage container, is provided at the bottle-side end of the bottle adapter. The index collar has an anesthetic-specific design, so that only the bottle adapter fitting the storage container can be screwed on the thread of the bottle.

An anesthetic-specific coding in the form of two projections, which are arranged offset at an angle in relation to one another and which engage corresponding openings on the filler neck of the filling device, is likewise provided on the adapter neck of the bottle adapter.

The outlet pipe of the bottle adapter is closed by means of a spring-loaded adapter valve, so that no anesthetic vapor can enter the environment. A corresponding filling valve is provided at the filling device. A stationary bar, whose length is selected to be such that the adapter valve can be opened during the introduction of the adapter neck into the filler neck of the filling device, is located in the middle of the filler neck of the filling device. The interaction between the bottle adapter and the filling device is designed such that the filling valve opens first and the adapter valve opens thereafter. Liquid anesthetic can then flow from the storage container into the tank of the anesthetic evaporator.

The drawback of the prior-art filling system is that the anesthetic-specific coding on the adapter neck can be introduced into the filler neck of the filling device in a certain preferred position only.

SUMMARY OF THE INVENTION

The basic object of the present invention is to simplify a filling system of the type in terms of its construction such that the anesthetic-specifically coded adapter neck of the bottle adapter can be introduced into the filler neck in a simple manner.

According to the invention, a filling system is provided for an anesthetic evaporator. The filling system comprises a bottle adapter for connection to a storage container for liquid anesthetic. The bottle adapter has an adapter neck. An outer polygon is provided as an anesthetic-specific coding on said adapter neck. A filling device for anesthetic is provided at the anesthetic evaporator with a filler neck for receiving the adapter neck. The filler neck has an inner polygon as an anesthetic-specific coding, which has a design corresponding to that of the outer polygon.

The polygon is preferably designed as a regular n-sided polygon. A hexagon, a pentagon or a heptagon may be employed as the polygon.

The anesthetic-specific coding designed as a polygon, preferably as a regular n-sided polygon may with different polygons for different anesthetics. For example, a hexagon may be selected as the polygon for the anesthetic halothane, a regular pentagon for enflurane, and a regular heptagon for isoflurane. Thus, no special preferred position is to be complied with for introducing the bottle adapter into the filling device, but the introduction position can be found by slightly rotating the bottle adapter in relation to the filling device.

The filling system is such that the bottle adapter is rigidly connected to the storage container.

An exemplary embodiment of the present invention is shown in the figures and will be explained in greater detail below.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENTS

Figure 1:
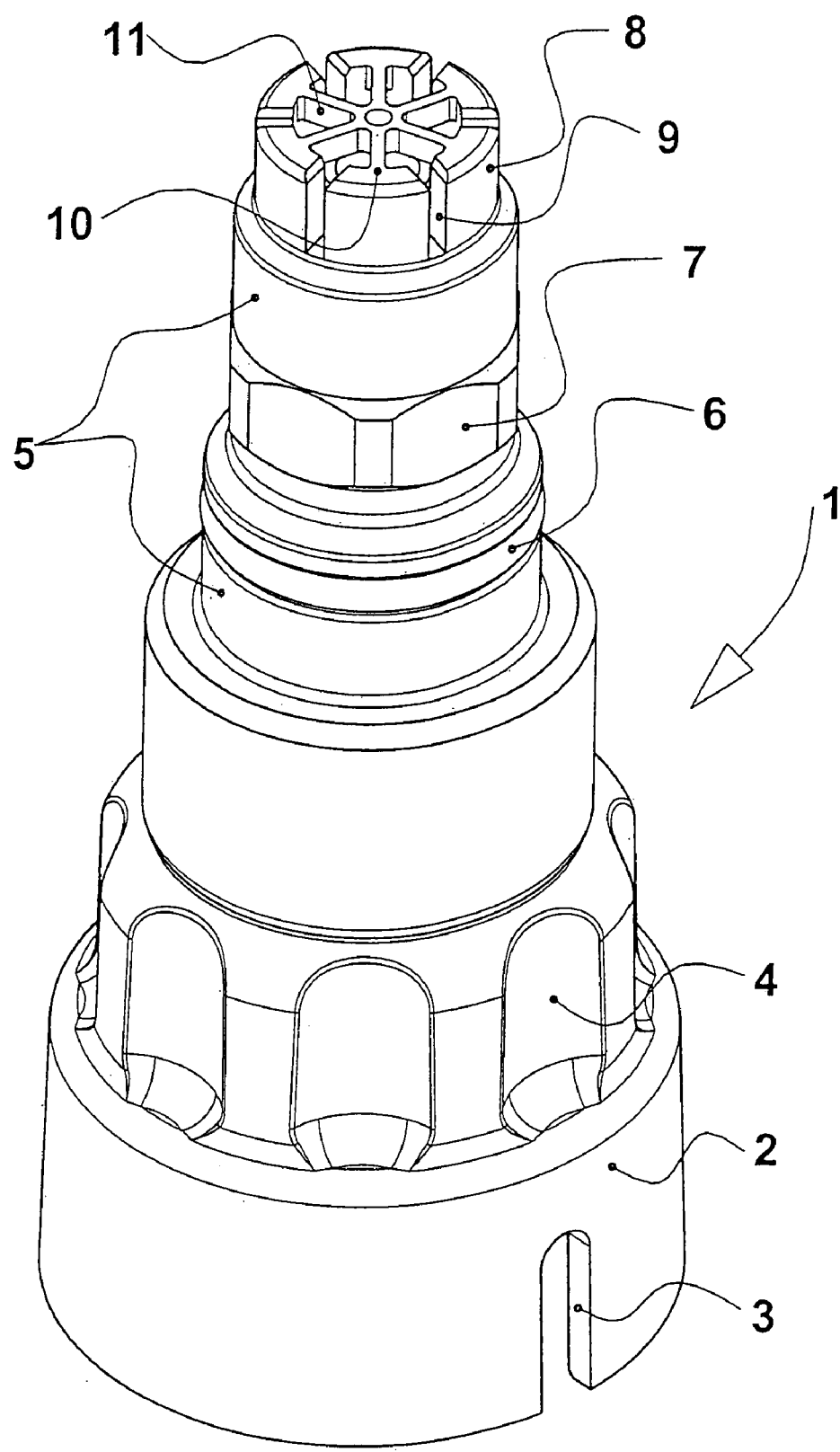
FIG. 1 is a perspective view of a bottle adapter.

Referring to the drawings in particular, FIG. 1 shows a perspective view of a bottle adapter 1, which has a collet 2 on its underside for being screwed on a storage container for liquid anesthetic, not shown in FIG. 1. On its bottle collar, the storage container has an anesthetic-specific index collar, which is introduced into receiving grooves 3 of the collet 2. Thus, only a bottle adapter 1 that belongs to the anesthetic can be screwed onto the storage container. The screwing movement is facilitated by recessed grips 4 above the collet 2. An adapter neck 5 with an O-ring 6 and with an outer polygon 7 for the anesthetic-specific coding as well as an outlet neck 8 with radially extending slots 9 is located at the upper end of the bottle adapter 1. The top side 10 of the neck is designed as a star 11.

Figure 2:
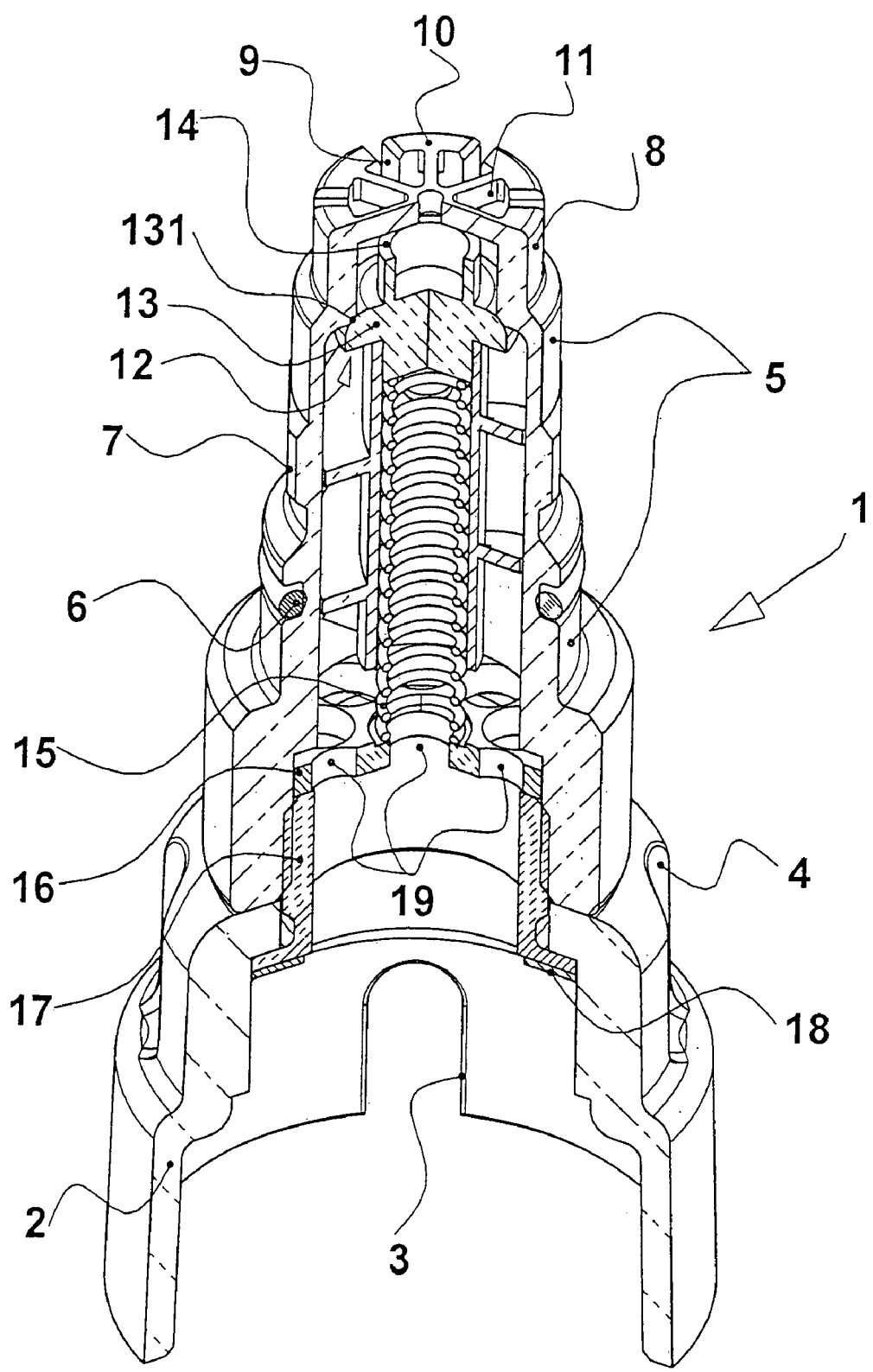
FIG. 2 is a longitudinal sectional view of the bottle adapter according to FIG. 1.

FIG. 2 illustrates the bottle adapter 1 according to FIG. 1 in a longitudinal section. Identical components are designated by the same reference numbers as in FIG. 1. A shut-off valve 12 with a valve piston 13, a ring 14 on the top side of the valve piston 13 and with a valve spring 15, which is pretensioned by means of a support plate 16 and presses the valve piston 13 against a sealing surface 131, is located within the bottle adapter 1. The support plate 16 is held within the bottle adapter 1 by a support cage 17. A sealing washer 18, which lies on the bottle neck of the storage container, not shown in the figures, is fastened on the underside of the support cage 17. The support plate 16 contains holes 19, via which the exchange of gas and liquid takes place. The polygon 7 has an anesthetic-specific design, e.g., a hexagon for halothane, a regular pentagon for enflurane, and a regular heptagon for isoflurane.

Figure 3:
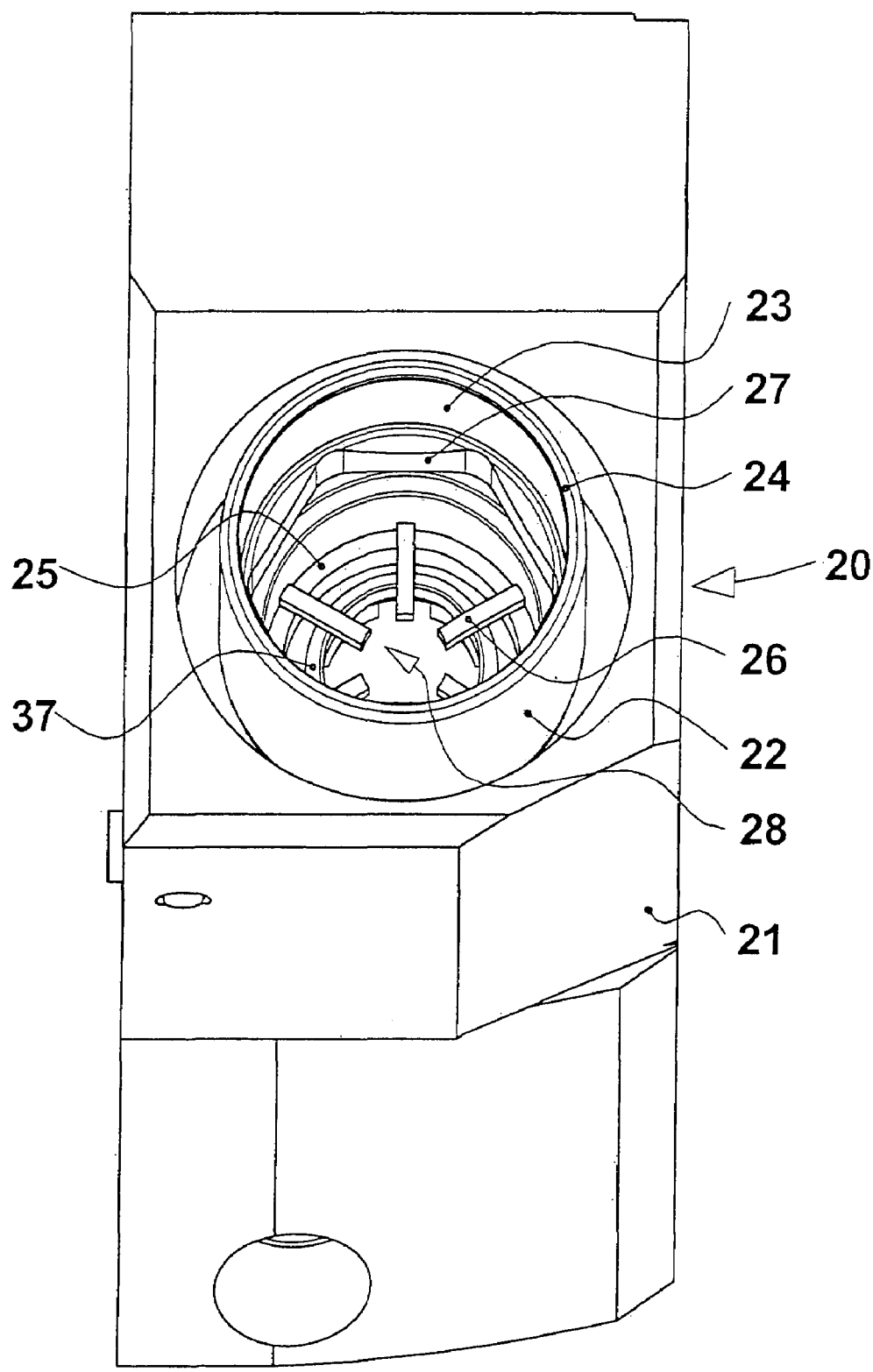
FIG. 3 is a perspective view of a filling device.

FIG. 3 shows a perspective view of a filling device 20 for anesthetics at an anesthetic evaporator 21. A filling device 20 has a filler neck 22 with a cylindrical sealing surface 23, an inner lead-in bevel 24 at the upper end of the filler neck 22, a spoked wheel 25 with radially inwardly pointing bars 26, an inner polygon 27 for the anesthetic-specific coding, and a filling valve 28.

Figure 4:
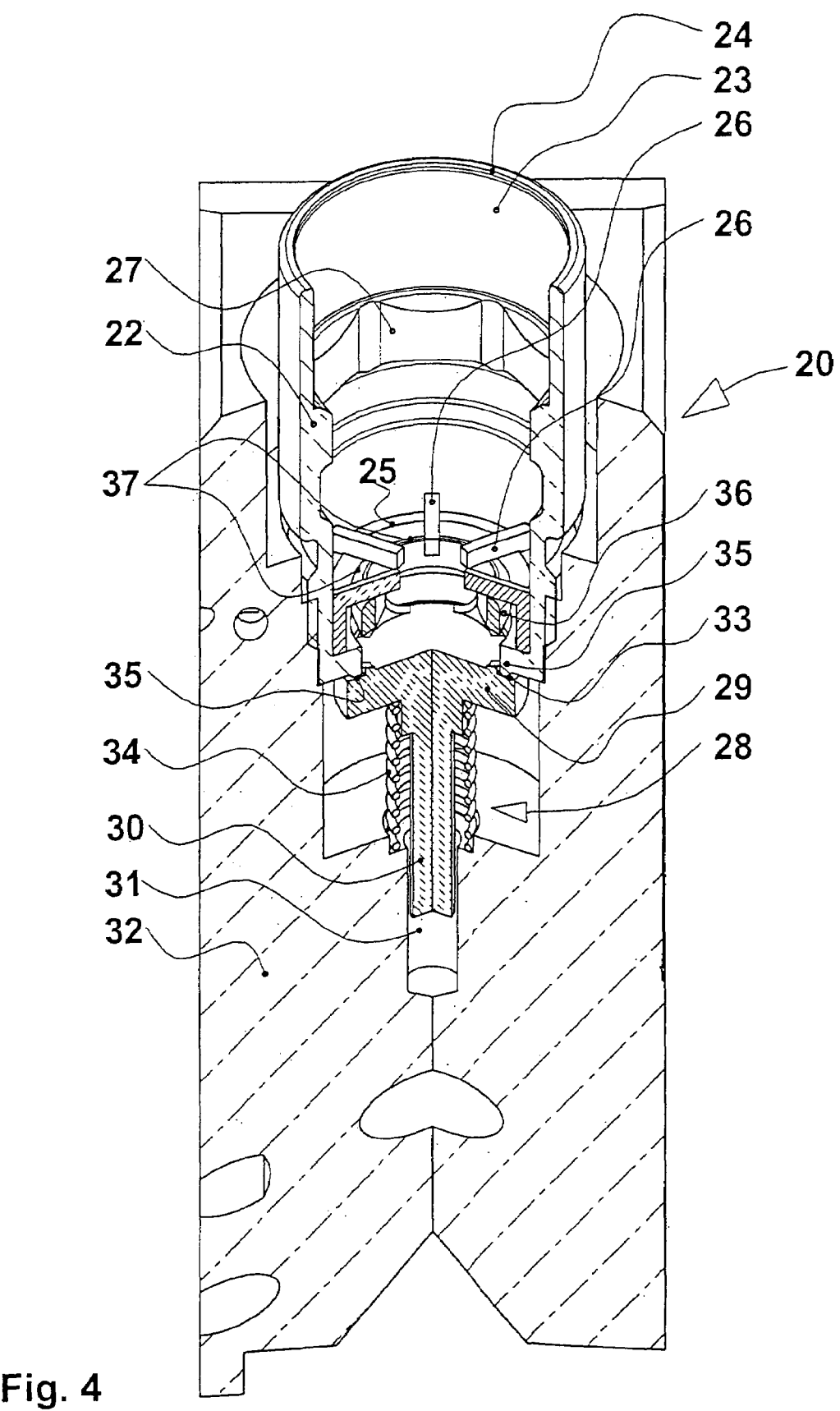
FIG. 4 is a longitudinal sectional view of the filling device according to FIG. 3.

FIG. 4 illustrates a longitudinal section of the filling device 20. Identical components are designated by the same reference numbers as in FIG. 3. The filling valve 28 comprises a valve plate 29 at a valve guide bar 30, which is received in a hole 31 of the evaporator housing 32 in such a way that it can perform lifting movements. The top side 33 of the valve plate 29 is pressed by means of a valve spring 34 against a sealing crater 35 of the filling valve 28. A guide ring 36 is connected with the valve plate 29 and can be displaced together with the valve plate 29.

The filling system according to the present invention operates as follows:

When the bottle adapter 1 is plugged into the filling device 20, the O-ring 6 first slides over the lead-in bevel 24 and is in contact with the sealing surface 23 of the filler neck 22. The outer polygon 7 will later engage the inner polygon 27 and the bottle adapter 1 is centered in relation to the filling device 20 as a result. The rods or bars 26 will then be located in the slots 9 of the outlet neck 8 and the outlet neck 8 will enter the area of the guide ring 36.

Due to the bottle adapter 1 being pressed, the neck top side 10 of the bottle adapter is in contact with the top side 37 of the guide ring 36 and the filling valve 28 opens. The adapter valve 12 is still closed. If the pressure on the bottle adapter 1 is increased further, the valve plate 29 is displaced against the force of the valve spring 34 farther downward and the bars 26 touch the ring 14 of the valve body 13, as a result of which the adapter valve 12 opens. Anesthetic is now flowing from the storage container via the holes 19 of the support plate 16 into the tank of the anesthetic evaporator and, as in communicating vessels, gas flows back into the storage container via the holes 19 from the tank.

When the filling operation is terminated, the adapter valve 12 closes at first, so that possible residual quantities of anesthetic within the filler neck 22 can flow off into the tank of the anesthetic evaporator 21. The filling valve 28 is then closed and the bottle adapter 1 can be removed from the filler neck 22.

While a specific embodiment of the invention has been shown and described in detail to illustrate the application of the principles of the invention, it will be understood that the invention may be embodied otherwise without departing from such principles.

What is claimed is:

1. A filling system for an anesthetic evaporator, the filling system comprising:
    a plurality of bottle adapters for connection to storage containers for liquid anesthetic, each of said bottle adapters having an adapter neck, each of said adapter necks including an adapter valve and an outlet neck, each said outlet neck defining slots;
    a plurality of different outer polygons as an anesthetic-specific coding, each of said plurality of outer polygons being arranged on one of said adapter necks;
    a plurality of filling devices for anesthetic, each of said plurality of filling devices being disposed at the anesthetic evaporator and having a filler neck for receiving one of said adapter necks, each of said filler necks having an inner polygon as said anesthetic-specific coding on a respective said filler neck with a design corresponding to one of said plurality of outer polygons, each said outer polygon is positionable in a corresponding said inner polygon in a plurality of different positions, a filling valve is arranged in each of said filler necks, a plurality of bars extend radially inward from an inner surface of said each filler neck, said bars correspond to said slots in a corresponding said outlet neck, said bars, said outlet neck, said adapter valve and said filling valve being arranged to have said outlet neck open said filling valve and to have said bars open said adapter valve when said adapter neck is inserted into said filler neck.

2. A filling system in accordance with claim 1, wherein said inner and outer polygons are designed as a regular n-sided polygons.

3. A filling system in accordance with claim 2, wherein a hexagon, a pentagon or a heptagon are provided as said polygons.

4. A filling system in accordance with claim 1, wherein said each bottle adapter is adapted to be rigidly connected to said storage container.

5. A filling system for an anesthetic evaporator, the filling system comprising:
    a plurality of liquid anesthetic storage containers;
    a plurality of bottle adapters each connected to one of said liquid anesthetic storage containers, each said bottle adapter having an adapter neck with an outer surface providing a different outer polygon defining an anesthetic-specific coding on said adapter neck, each of said adapter necks including an adapter valve and an outlet neck, each said outlet neck defining slots;
    an anesthetic evaporator;
    a plurality of filling devices for filling the anesthetic evaporator with anesthetic, each said filing device being disposed at said anesthetic evaporator and having a filler neck for receiving said adapter neck, each said filler neck having an inner polygon as said anesthetic-specific coding on said each filler neck with a shape corresponding to one of said outer polygons, each of said outer polygons is positionable in a respective said inner polygon in a plurality of different positions, a filling valve is arranged in each of said filler necks, a plurality of bars extend radially inward from an inner surface of said each filler neck, said bars correspond to said slots in a corresponding said outlet neck, said bars, said outlet neck, said adapter valve and said filling valve being arranged to have said outlet neck open said filling valve and to have said bars open said adapter valve when said adapter neck is inserted into said filler neck.

6. A filling system in accordance with claim 5, wherein said polygons are designed as a regular n-sided polygon.

7. A filling system in accordance with claim 6, wherein a hexagon, a pentagon or a heptagon are provided as said polygon.

8. A filling system in accordance with claim 5, wherein said bottle adapter is rigidly connected to said storage container.

9. A filling system in accordance with claim 5, wherein:
    said outlet neck opens said filling valve before said bars open said adapter valve.

10. A filling system in accordance with claim 5, wherein:
said bars align with, and are insertable into, said slots in said plurality of different positions.

11. A filling system in accordance with claim 1, wherein:
said outlet neck opens said filling valve before said bars open said adapter valve.

12. A filling system in accordance with claim 1, wherein:
said bars align with, and are insertable into, said slots in said plurality of different positions.

13. A filling system for an anesthetic evaporator, the filling system comprising:
  a bottle adapter for connection to a storage container for liquid anesthetic, said bottle adapter having an adapter neck;
  an outer polygon as an anesthetic-specific coding on said adapter neck;
  a filling device for anesthetic, said filing device being disposed at the anesthetic evaporator and having a filler neck for receiving said adapter neck, said filler neck having an inner polygon as said anesthetic-specific coding on said filler neck with a design corresponding to that of said outer polygon;
  an adapter valve in said adapter neck;
  a filling valve in said filler neck;
  an outlet neck is arranged on said adapter neck, said outlet neck defining slots;
  a plurality of bars extend radially inward from an inner surface of said filler neck, said bars corresponding to said slots in said outlet neck;
  said bars, said outlet neck, said adapter valve and said filling valve being arranged to have said outlet neck open said filling valve and to have said bars open said adapter valve when said adapter neck is inserted into said filler neck.

14. A filling system in accordance with claim 13, wherein:
said outlet neck opens said filling valve before said bars open said adapter valve.

15. A filling system in accordance with claim 13, wherein:
said outer polygon is positionable in said inner polygon in a plurality of different positions.

16. A filling system in accordance with claim 15, wherein:
said bars align with said slots in said plurality of different positions.

17. A bottle adapter for connecting a storage container for liquid anesthetic with a filling device of an anesthetic evaporator, said adapter comprising:
  an adapter neck including an adapter valve and an outlet neck, said outlet neck defining slots;
  an anesthetic specific coding on said adapter neck, said coding being selected of a plurality of different anesthetic specific outer polygons;
  the filling device comprising an inner neck,
  an anesthetic specific coding on said inner neck, said coding being selected of a plurality of different inner polygons with a design corresponding to said outer polygons, a filling valve is arranged in said inner neck, a plurality of bars extend radially inward from an inner surface of said inner neck, said bars correspond to said slots in said outlet neck, said bars, said outlet neck, said adapter valve and said filling valve being arranged to have said outlet neck open said filling valve and to have said bars open said adapter valve when said adapter neck is inserted into said inner neck.

* * * * *